United States Patent [19]
Millner et al.

[11] Patent Number: 5,089,016
[45] Date of Patent: Feb. 18, 1992

[54] BLOOD PUMP

[75] Inventors: Alan R. Millner, Lexington; Meir Rosenberg, Salem; Fredric L. Milder, Brookline, all of Mass.

[73] Assignee: ABIOMED Cardiovascular, Inc., Danvers, Mass.

[21] Appl. No.: 366,860

[22] Filed: Jun. 15, 1989

[51] Int. Cl.⁵ ............................................. A61F 2/22
[52] U.S. Cl. ........................................................ 623/3
[58] Field of Search ..................... 623/3; 417/413, 394

[56] References Cited

U.S. PATENT DOCUMENTS

| | | | |
|---|---|---|---|
| 3,955,557 | 5/1976 | Takagi | 623/3 |
| 4,091,471 | 5/1978 | Richter | 623/3 |
| 4,250,872 | 2/1981 | Tamari | 417/394 |
| 4,468,177 | 8/1984 | Strimling | 623/3 |
| 4,755,111 | 7/1988 | Cocchi et al. | 417/394 |

FOREIGN PATENT DOCUMENTS

| | | | |
|---|---|---|---|
| 3725567 | 2/1989 | Fed. Rep. of Germany | 623/3 |
| 0055943 | 11/1988 | Japan | 623/3 |
| 8901765 | 3/1989 | World Int. Prop. O. | 623/3 |

Primary Examiner—David J. Isabella
Attorney, Agent, or Firm—Lahive & Cockfield

[57] ABSTRACT

A blood pump having a toroidal shaped chamber concentrically positioned around a cylindrically shaped hydraulic pump. The toroidal chamber has two toroidal shaped portions, one portion having a substantially rigid external wall and the other having an external wall formed of a flexible membrane. The chamber has an inlet and output port suitable for connection to a blood flow supply. The flexible wall portion of the toroidal chamber is enclosed within a hydraulic chamber, fluidically coupled to the hydraulic pump. The hydraulic pump is controlled so that an increase of pressure in the hydraulic chamber results in a decrease of volume in the toroidal chamber, thus providing for pumping of the blood through that portion of the chamber. The toroidal shape provides for optimal non-coagulating flow, while the rigid wall of the chamber, together with the flexible membrane provide for membrane motion along only one axis, normal to the circumference of the toroid, preventing damage to the membrane. The blood flow inlet port is positioned to direct fluid in a tangential direction against the perimeter wall of the toroid.

13 Claims, 3 Drawing Sheets

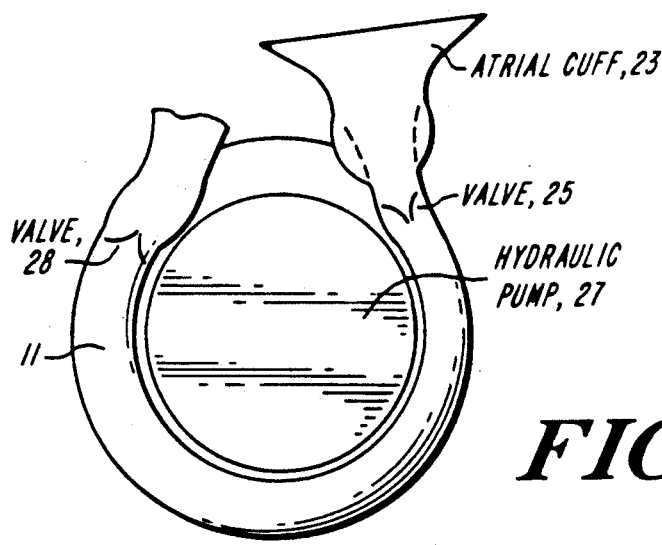
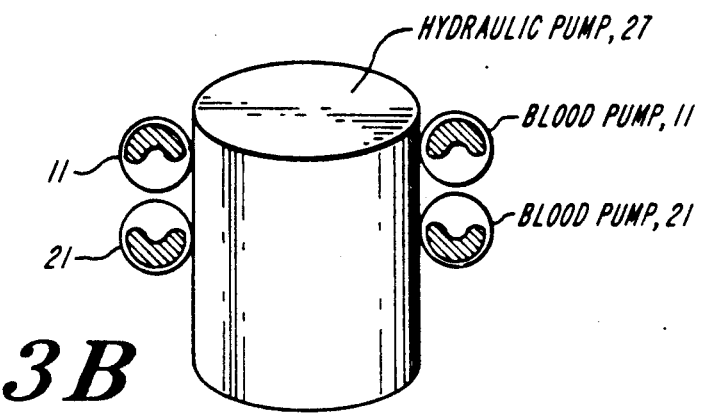
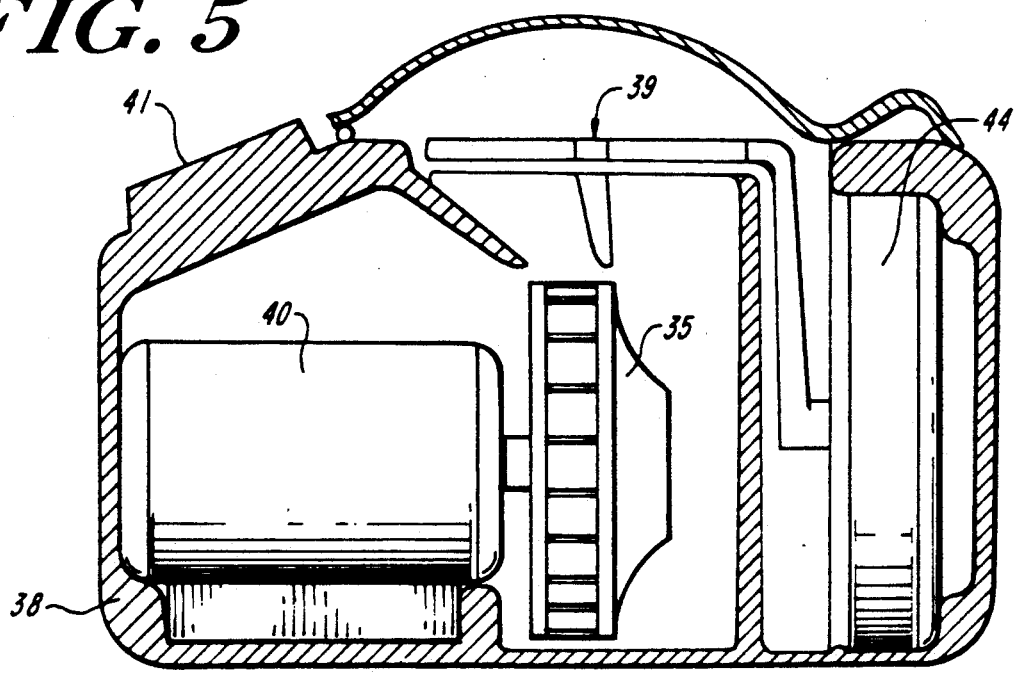

BLOOD PUMP

This invention was made with Government support under Contract Number N01-HV-88104 awarded by the National Institute of Health. The Government has certain rights in the invention.

BACKGROUND OF THE INVENTION

This invention relates in general to blood Pumps and more particularly to an implantable pump for replacement for a natural heart or for assistance to the pumping of the natural heart.

A number of designs have been developed for insertable blood pumps to replace or assist a natural heart. Typically such pumps are formed of a collapsible volume which can be filled and emptied with blood to provide pumping action. The shape has generally been ellipsoid with the mechanism for periodically collapsing the volume being pneumatic, hydraulic, or pusher plates. One such pump is the so-called Jarvik heart which employs a flexible membrane forming an inner wall of a rigid chamber, with the pumping being generated by hydraulic pressure against the flexible membrane controlled to provide appropriate stroke volume and repetition rate. Others include pumps with a roller screw, rotary cam, or magnetic actuator to actuate a pusher plate, and a high pressure pumping mechanism.

In many of these heart designs the blood is introduced into the chamber tangentially so that there is a generally rotary movement of the blood in the hemispherical chamber. Such an arrangement, coupled with the non-thrombogenic lining of the inner surface of the chamber is intended to inhibit clot formation. One problem, however, in this arrangement is that at the center of the vortex of the rotation there is a tendency for the blood to stagnate and thus provide a physical basis which can lead to formation of thrombosis. It has been suggested that a pump employing a toroidal shaped chamber completely formed of flexible material can avoid this Problem while still maintaining the generally circular flow of blood. One drawback to this configuration is the tendency of that flexible wall to kink or fold as it is contracted and expanded for pumping action. Such kinks or folds result in high local strain on the membrane material, thereby providing a limited lifetime for the pump.

It is therefore a primary object of the present invention to provide a fluid driven blood pump with a toroidal shape to avoid stagnation of portions of the blood by employing a toroidal shaped blood flow chamber.

It is another object of this invention to provide a blood pump for efficient circulation of blood employing hydraulic pumping wherein the parts of the chamber are constructed interpositioned to allow to provide for long component life.

It is finally an object of the present invention to provide a toroidal shaped Pump which not only wraps in Physical form conveniently around a cylindrical hydraulic actuator, but also provides for flexible membrane movement only on one axis, transverse to the direction of blood flow. This provides effective pump action with a toroidal blood flow, yet avoids kinking or folding, resulting in good fatigue characteristics and a long lifetime for the pump, as well as minimizing the formation of clots.

SUMMARY OF THE INVENTION

Broadly speaking, in the present invention a toroidal shaped blood pumping chamber is formed with one rigid exterior wall and includes a flexible membrane wall sealed to the rigid wall thereby forming a toroidal chamber with a rigid upper one half toroid and a flexible membrane lower half toroid. This toroidal chamber has at least its flexible portion enclosed within a fluid pressure chamber, which may be either pneumatic or hydraulic and is coupled to a suitable pneumatic or hydraulic pump. Fluid is pumped into and out of the pressure chamber with a controlled periodic variation in pressure to provide blood Pumping action by driving the membrane to move only along an axis transverse to the direction of flow of the blood. The toroidal chamber is tangentially coupled to the blood supply in the inlet port and provides blood flow from a tangentially coupled outlet port into the circulatory system.

This configuration provides the advantages of toroidal flow of having no stagnant center Portion, while the unidirectional movement of the membrane provides for long life for this component. The toroidal chamber may conveniently be wrapped around a cylindrically formed hydraulic actuator to provide a compact package. In practice, the moving and stationary walls of the toroidal blood chamber are formed of one seamless elastomer material.

DESCRIPTION OF THE DRAWINGS

In the drawings:

FIG. 3a is a plan view of a blood pumping chamber assembled around a hydraulic pumping unit;

FIG. 3b is an illustration partially in perspective and partially in cross sectional view of the blood pump assembly of FIG. 3a showing a pair of blood pumps positioned around the hydraulic pump unit;

FIG. 5 is a cross sectional view of the hydraulic pump of FIG. 4 in a plane perpendicular to the plane of FIG. 4.

DESCRIPTION OF PREFERRED EMBODIMENTS

Figure 2:
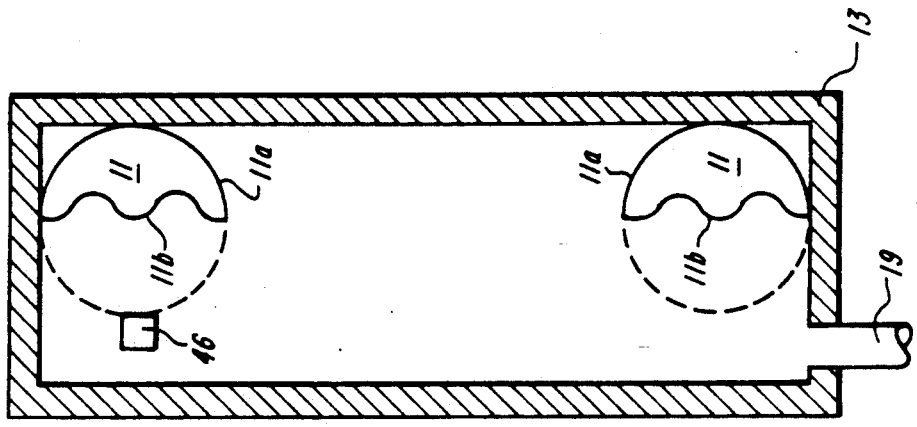
FIG. 2 is an illustration in cross sectional view of the pumping chamber of FIG. 1.
Figure 1:
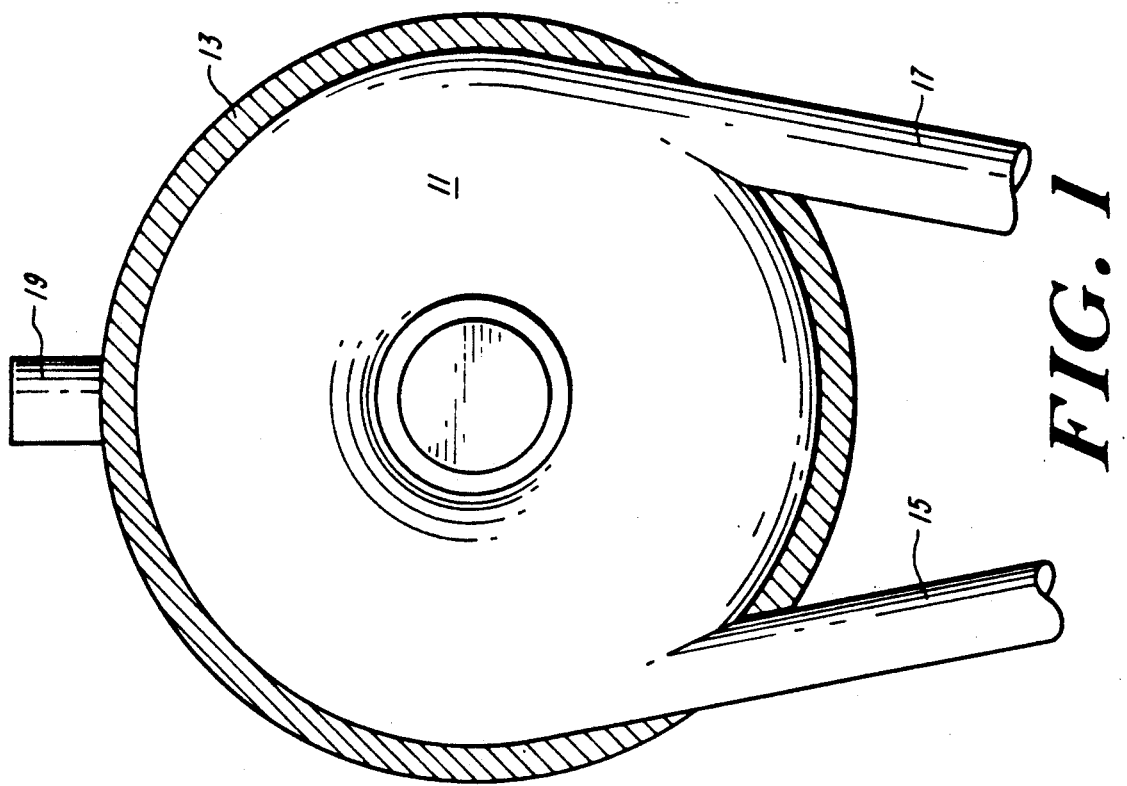
FIG. 1 is a plan view of a pumping chamber constructed in accordance with the principles of this invention.

With reference now to FIGS. 1 and 2, a toroidal shaped blood pumping chamber 11 is formed with a rigid wall forming the upper half and a flexible membrane 11b forming the lower half of the toroid chamber 11. The chamber includes an inlet port 15 and an outlet port 17, each coupled to the rigid portion of the chamber at an angle such that blood flow into and out of the chamber is tangential to the circumference of the chamber. The entire toroidal chamber 11 is immersed within a rigid walled pressure chamber 17 which has a fluid input port 19, which is out of the moving plane of the flexible membrane 11b. In this embodiment the pressure chamber is a hydraulic chamber.

In operation, a hydraulic pump 27, as illustrated in FIGS. 3a and 3b is coupled to the hydraulic input port 19 to provide in controlled Periodic cycles, increases and decreases of pressure within it thereby causing the flexible membrane 11b to flex in a direction generally parallel to the axis of the toroid, thereby decreasing and increasing the volume enclosed by the rigid wall 11a and the flexible membrane 11b. In general the these increases and decreases in pressure should be substantially evenly applied around the toroid and the membrane 11b should flex only in the direction parallel to the axis.

A suitable material for the toroid has been found to be thin (between approximately 0.25 and 0.5 mm) polyurethane formed into a generally toroidal shape. In order to provide for the rigid portion of the toroidal chamber, approximately half of the toroid is coated with a suitable epoxy such as Stycast Epoxy 1267 manufactured by Emerson & Cummings, Woburn, Masssachusetts, which can have a thickness any where from 0.2 to 5.0 mm, thereby providing for a completely sealed chamber having a rigid wall and a flexible membrane wall. The free length of the membrane should be sufficient to allow full collapse but not long enough to cause folds. Suitable dimensions for the chamber 11 include a displaced volume of 70 cubic cm, an outer diameter of approximately 10 cm and an inner diameter of the toroid of approximately 5.5 cm. Alternatively the rigid portion may be formed of a thicker walled section of elastomer.

As illustrated in FIGS. 3a and 3b hydraulic pump 27 may be fabricated in a generally cylindrical form and appropriately valved to provide for controlled pulsatile flow of hydraulic fluid into and out of the hydraulic chamber 13.

As is shown, particularly in FIGS. 3a and 3b, the toroidal chamber 11 is coupled through its inlet and outlet port and one-way leaflet valves 25 and 28 to provide for blood flow, in this instance in a clockwise fashion around the toroid. In a total implanted heart configuration, the valve 25 would be placed at the outlet of an atrial cuff 23 which can be sewn to the portion of the circulatory system which, in a natural heart, would be coupled to one of the atria of the natural heart. In either instance the valves are located out of the plane of the flexing part of the torus so that they do not distort its shape. The blood outflow through valve 28 would be coupled to either the aorta or the pulmonary artery in an individual circulatory system. Artificial valves suitable for this purpose are known in the art. One particularly suitable type of valve is described in U.S. Pat. application Ser. No. 06/720,361, filed May 1, 1985 and entitled Prosthetic Heart Valve. Mechanical valves such as those manufactured by Bjork-Shively Medronic-Hill or St. Jude Corp. could also be utilized. In general, in this configuration the displaced volume. Of the toroidal chamber is approximately 70 cubic cm with an effective stroke volume in the pumping made of 60 cubic cm. The inner diameter of the inlet and outlet ports is approximately 20 to 25 mm, which is compatible with a 25 mm diameter artificial leaflet valve.

The pressure waveform in the hydraulic fluid will then reflect the pressure in the blood vessels accessed by the open valve. It takes the form of an approximately rectangular wave, with Pressure during systole equal to the arterial pressure supplied by the ventricle, and pressure during diastole equal to the central venous pressure filling the blood pump. These pressure waves may be sampled at appropriate times with a pressure sensor to obtain signals for control of the hydraulic fluid pump speed.

In FIG. 3b a second toroidal blood pump 21 is shown positioned around the hydraulic pump so that the total assembly would provide for both right and left ventricle pumping. As will be described in more detail below, the hydraulic pump 27 can be arranged so that the hydraulic pressure is valved and applied alternately to blood pump 11 or blood pump 21.

Figure 4:
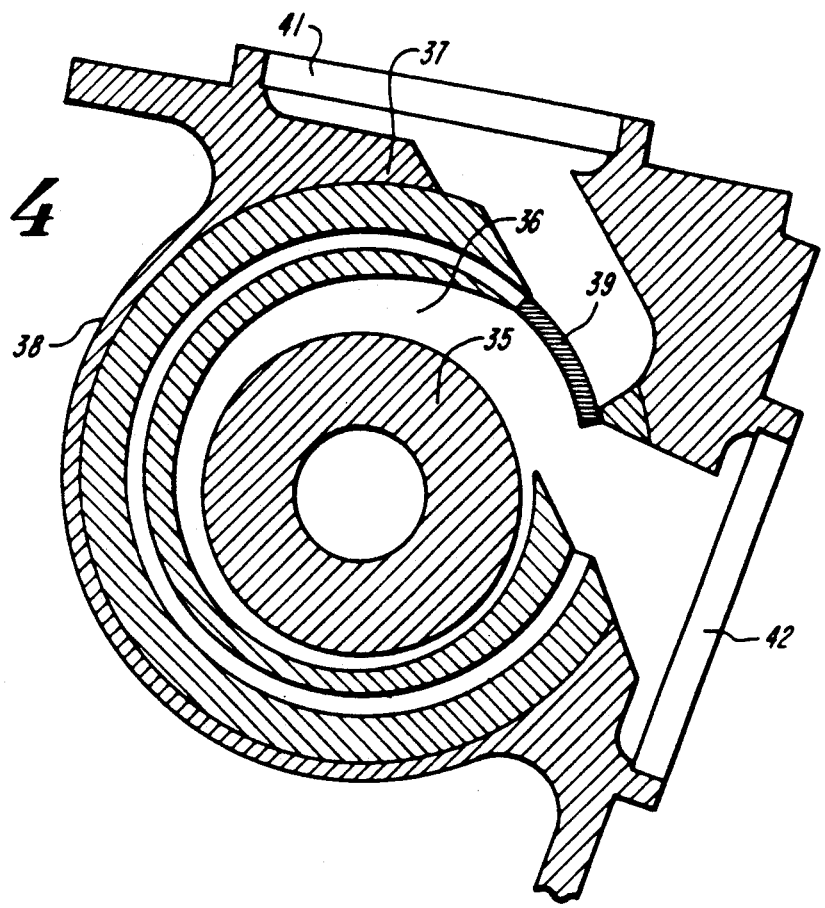
FIG. 4 is a cross sectional view of one embodiment of a hydraulic pump suitable for use in the practice of this invention.

A particularly suitable pump for operating this toroidal blood pump has been found to be a centrifugal pump. Such a pump is illustrated in FIGS. 4 and 5. The hydraulic pump includes an electrical pump motor 40 which drives impeller 35 to produce flow of the hydraulic fluid contained within the cavity 36 formed by housing 38. The valving action is accomplished by a rotating valve 39 driven by a valve motor 44 to control the hydraulic fluid output flow to pass alternately through hydraulic output ports 41 and 42. One of these outlet ports, for example, port 41, may be coupled to toroidal chamber 11, while the other would be coupled to toroidal chamber 21.

A suitable electric motor for driving a centrifugal pump of this design is that manufactured by Inland Motor of Sierra Vista, Arizona under the name RBE Motor Series. A suitable beat rate is slightly faster than the natural heart, for example, 80 to 160 beats per minute. To accomplish the control function, it may be desirable to have a sensor 46 sensing the spacing between the membrane 11b and the rigid wall 11a of the toroidal cavity. This sensor may, for example, be an optical sensor providing an output signal indicative of the variation of this spacing as a measure of the change in stroke volume to a suitable electrical control circuit (not shown).

Figure 6:
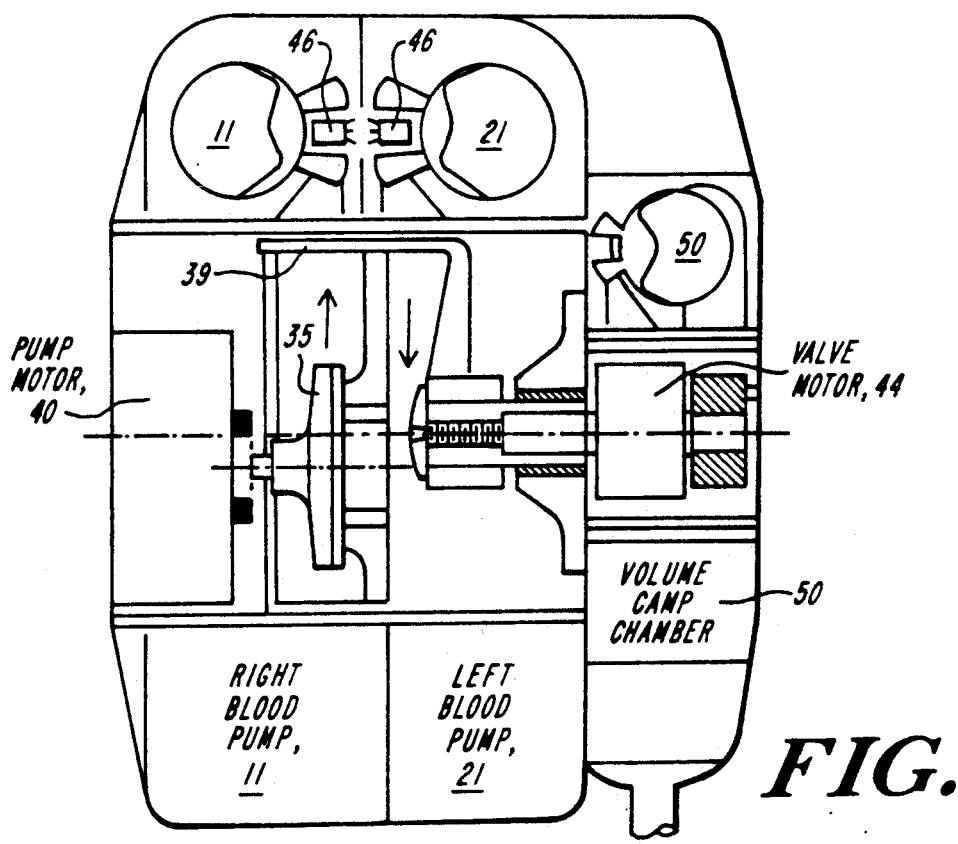
FIG. 6 is a generally diagrammatic view of the blood pump assembly constructed in accordance with the principles of this invention.

In FIG. 6 there is illustrated an appropriate configuration for a total artificial heart employing the toroidal chamber and a centrifugal hydraulic pump. In FIG. 6 like numbers refer to like parts of the previous figures. Also included in the artificial heart configuration of FIG. 6 is an additional volume compensation chamber 50, also formed as a toroidal chamber which can be hydraulically coupled to the hydraulic chamber of the right blood pump 11 and fluidically coupled to the blood volume 11 in the left atrium, which is valved into the left blood pump 21 to provide for asymmetrial pumping of the left and right ventricles of the artificial heart. A pump of the configuration of FIG. 6 can be formed with an outer dimension of the toroidal chambers of less than 11 cm with axial dimension of less than 9 cm.

Having described the invention it will be realized that the pump may be formed of different materials and in different configurations. For example, the hydraulic pump and valves may be reciprocally operating rather than rotationally. The operation may be accomplished pneumatically, with pressurized gas, as is done in the Jarvik heart, as well as hydraulically utilizing a liquid. Another actuation method is by mechanical means in the form of a ring push plate attached to the flexing portion of the toroidal pump. The invention is set forth in the following claims.

What is claimed is:

1. A fluid driven blood pump apparatus comprising,
a fluid pump having an outlet port,
a toroidal shaped blood pumping chamber having a major and minor axis divided into first and second axial toroidal shaped portions by a plane perpendicular to the major axis, said first axial toroidal shaped portion comprising a rigid wall and said second axial toroidal shaped portion being formed of a flexible membrane in sealed relation to said first axial toroidal portion, said toroidal chamber having an inlet port positioned to couple blood into said toroidal chamber and an outlet port positioned to couple blood out of said toroidal chamber, a pressure chamber surrounding at least said second toroidal shaped portion of said toroidal chamber, the outlet port of said fluid pump being fluidically coupled to said pressure chamber such that increases in fluid pressure from fluid pumped from said fluid pump into said pressure chamber flex said membrane to decrease the blood volume within said toroidal chamber, and decreases in fluid pressure within said pressure chamber flex said membrane to increase the blood volume in said toroidal chamber, said fluid increases and decreases within said chamber being substantially evenly applied around said toroidal chamber so that said flexible membrane is flexed only substantially along one axis parallel to the major axis of said toroid.

2. An apparatus in accordance with claim 1 wherein said fluid is hydraulic fluid and said fluid pump is a hydraulic pump.

3. An apparatus in accordance with claim 2 having a one-way fluid valve coupled to said inlet port permitting blood flow only into said toroidal chamber through said inlet port and having a one-way valve at said toroidal chamber outlet port permitting blood flow only out from said toroidal chamber through said toroidal chamber outlet port.

4. An apparatus in accordance with either of claims 2 or 3 and further including control means to control said hydraulic pump to provide pulsatile stroking of said blood pump apparatus.

5. An apparatus in accordance with either of claims 2 or 3 where said entire toroidal chamber is formed of a flexible polyurethane, wherein a portion of said membrane has been made rigid by application of a rigid polymeric material on the outside surface of said portion of said membrane.

6. An apparatus in accordance with either of claims 2 or 3 where said entire toroidal chamber is formed of a flexible elastomeric membrane wherein a portion of said membrane has been made rigid by forming said portion of the membrane with a thicker wall than the remaining portion.

7. An apparatus in accordance with claim 3 wherein the interior surface of said toroidal chamber is formed of a material which is non-injurious to blood flowing therethrough and wherein said toroidal chamber inlet and outlet ports are adapted to be coupled to a blood circulatory system of a patient.

8. Apparatus in accordance with claim 2 wherein said fluid pump is enclosed within a generally cylindrical casing, the cylindrical casing having a curved outer surface with an outer circumference substantially equal to the inner circumference of said toroidal shaped blood pumping chamber, wherein said toroidal shaped blood pumping blood is placed around the curved outer surface of said cylindrical casing, generally concentric with the longitudinal axis thereof.

9. An apparatus in accordance with claim 7 and further including a second toroidal shaped blood pumping chamber having first and second axial toroidal shaped portions to the first and including a second pressure chamber surrounding at least said second axial toroidal shaped portion of said second toroidal chamber, and wherein said fluid pump includes valving means for alternately providing fluid pressure to the pressure chamber surrounding at least said second axial toroidal shaped portion of said first toroidal chamber and to said second pressure chamber, and control means for controlling said valve operation to provide said alternate hydraulic pressure application in a predetermined time sequence.

10. A blood pump apparatus in accordance with claim 1 wherein said flexible membrane is sealed to the inner and outer edges of said rigid wall.

11. A blood pump apparatus in accordance with any one of claims 1, 2 or 10 wherein said inlet and outlet ports are positioned axially displaced from said plane perpendicular to the major axis of said toroid on said first axial toroidal shaped portion at an angle such that the blood flow into and out of the chamber, if projected onto said plane, is tangential to the circumference of said chamber.

12. Apparatus in accordance with claim 9 wherein said fluid pump is enclosed within a generally cylindrical casing having a curved outer surface with an outer circumference substantially equal to the inner circumference of said toroidal shaped blood pumping chamber, wherein said toroidal shaped blood pumping chamber is placed around the curved outer surface of said cylindrical casing, generally concentric with the longitudinal axis thereof.

13. An apparatus in accordance with claim 12 and further including a toroidal shaped volume compensation chamber fluidically coupled to said second toroidal chamber.

* * * * *